United States Patent [19]

McArdle

[11] Patent Number: 5,747,416

[45] Date of Patent: May 5, 1998

US005747416A

[54] HERBICIDAL AND INSECTICIDAL PROTEIN-POLYSACCHARIDE DELIVERY COMPOSITIONS AND METHODS FOR CONTROLLING PLANT AND INSECT POPULATIONS

[76] Inventor: Blaise McArdle, 17 Leonard St., Annisquam, Mass. 01930-1321

[21] Appl. No.: 699,578

[22] Filed: Aug. 16, 1996

Related U.S. Application Data

[63] Continuation-in-part of Ser. No. 523,162, Sep. 5, 1995, Pat. No. 5,591,473, which is a continuation-in-part of Ser. No. 263,001, Jun. 17, 1994, abandoned, which is a continuation-in-part of Ser. No. 89,268, Jul. 8, 1993, abandoned.

[51] Int. Cl.$^6$ .............................. A01N 25/10; A01N 3/02; C05G 5/00
[52] U.S. Cl. ................ 504/115; 504/116; 514/773; 514/777; 514/950; 514/964
[58] Field of Search ............................. 504/116, 115; 71/DIG. 1; 514/773, 777, 950, 964

[56] References Cited

U.S. PATENT DOCUMENTS

| | | | |
|---|---|---|---|
| Re. 34,594 | 4/1994 | Christians | 504/116 |
| 4,007,258 | 2/1977 | Cohen et al. | 424/22 |
| 5,030,268 | 7/1991 | Christians | 71/122 |
| 5,290,749 | 3/1994 | Christians | 504/116 |
| 5,290,757 | 3/1994 | Christians | 504/335 |
| 5,356,467 | 10/1994 | Oshlack et al. | 106/153 |

*Primary Examiner*—S. Mark Clardy

[57] ABSTRACT

A protein-polysaccharide complex is used as a non-toxic and sustained release carrier for insecticides, herbicides, foliar nutrients and mixtures thereof. Methods for using a solution, solid or flowable impregnated protein-polysaccharide complex as a delivery agent for the control of plant populations and insect populations and as a preservative for cut flowers are described.

37 Claims, No Drawings ns to wind drift, while enhancing
HERBICIDAL AND INSECTICIDAL PROTEIN-POLYSACCHARIDE DELIVERY COMPOSITIONS AND METHODS FOR CONTROLLING PLANT AND INSECT POPULATIONS

RELATED APPLICATIONS

This is a continuation-in-part of my application entitled "Protein-polysaccharide Complex Composition, Method of Preparation and Use", Ser. No.08/523,162 filed on Sep.5, 1995, now U.S. Pat. No. 5,591,473, which is a continuation in part of Ser. No. 08/263,001, filed Jun. 17, 1994, abaondoned, which is a continuation in part of Ser. No. 08/089,268, filed Jul. 8, 1993, abandoned.

BACKGROUND OF THE INVENTION

1. Field of the Invention

The present invention relates to the use of a protein-polysaccharide complex as a delivery composition for plant protection agents having excellent formulation flexibility, controlled release potential, run-off resistance and hydrodynamic properties.

2. Description of the Prior Art

Infestations of weeds and insects have caused detrimental effects on health, agriculture, commerce, and recreation in many areas of the United States and overseas. When present in high densities, weeds can literally choke agricultural plantings, lakes and rivers and insects can carry a variety of diseases. In addition, in aqueous environments these weeds can disrupt the functioning of drainage, irrigation, flood control and water conservation projects and hydroelectric power plants, provide breeding grounds for disease carrying mosquitoes and snails, eliminate fishing in certain areas, and alter aquatic ecosystems by preventing sunlight from reaching other plants and animals which live beneath these vegetative mats. Therefore, the growth of these nuisance plant and accompanying insect populations must be controlled.

Solid and liquid herbicide and insecticide formulations designed for quick and slow or controlled release of the active ingredients are currently in use to control plants and insects; however, new formulations are needed that can enhance the efficacy and/or extend the range of performance of existing products.

A relatively new approach to herbicidal delivery has been by application of controlled release formulation such as described by Richard W. Baker in Controlled Release of Biologically Active Agents, 1987, Wiley-Interscience Publishing, 279 pp. This book describes the use of various controlled release technologies including simple diffusion from monolithic devices such as hydrogels. More complex release mechanism include the use of biodegradable matrix carriers, bonding of active ingredients in heterogeneously or homogeneously degradable polymers, called polyagents. Polyagents may actually be polymers formed of monomers of the active agent. The release mechanics of these controlled release mechanisms are complex depending on the presence (and strength) or absence, of degradable ligand bonds and their location of the degradable bonds (e.g., as active agent bonds to the polymer), the concentration of the active agent and/or dispersant or solvent in the carrier, the relative hydrophobicity or hydrophilicity of the polymer, whether or not the polymer degrades homogeneously or heterogeneously, whether the active agent is in the solid form or the liquid form in the polymer, etc.

It is known to add compounds, such as common salt, acetylsalicylic acid, 1-phenyl-4-dimethylamino-2,3-dimethyl-pyrazolone-(5) or also amino acids, such as N-(2-hydroxyethyl)-beta-alanine to the water used for the preservation of cut flowers. Aluminum sulfate and disaccharides have also already been used. The effect of these additions does not substantially lengthen the duration of the flowers for suitable presentation or appearance. There are also considerable differences in the degree of preservation in using these preserving agents depending upon the type of flower utilized.

A relatively new class of protein-polysaccharide complexes has recently been introduced that exhibits remarkable stabilizing properties in products such as asphalt. However, there has been no recognition of their uses as a delivery system for plant protection agents such as herbicidal; foliar nutrients, including preservation agents; and insecticidal compositions.

It is therefore an object of the present invention to provide compositions that are liquid, solid or flowable, and methods for the dry, moist, semi-aquatic, or aquatic ground or aerial treatment of a variety of plant (weed) or insect habitats with the composition, which overcomes the problems and deficiencies of the prior art.

It is also an object of the present invention to provide a composition and method, which is easy to prepare (formulate) and use (apply), and which is biodegradable and safe to the environment, but which is effective for use in controlling one or more immature and mature stages of obnoxious or undesirable insects and weeds or related vegetation.

It is a further object of the present invention to provide an agglomerated or non-agglomerated solid or variable-viscosity, flowable (aqueous or oil base) composition and method which can incorporate a wide variety of plant protection agents including herbicidal, pesticidal and foliar nutrient compositions and combinations thereof into a single, stable and homogeneous delivery system to control or treat a broad spectrum of insects and/or plant populations and other related habitat pests, and to provide for the variable time release of the active ingredients.

Still another object of the present invention is to provide a method for simultaneously or concurrently controlling two or more natural populations of vegetation, and habitat-related pests with a single, variable-density and/or herbicidal/pesticidal carried on a protein-polysaccharide complex carrier or matrix delivery formulation.

Still another specific object of the present invention is the provision of incorporating one or more surfactant(s), oil(s), surface-active agent(s) or film-forming agent(s) into a stable and homogeneous, variable-viscosity, flowable plant protection agent and protein-polysaccharide complex formulation, the addition of which can slow the rate of release of one or more active ingredients in the plant protection agent delivery composition.

Still another object of the present invention is to provide a method for independently, simultaneously or concurrently controlling or treating natural populations of plants and habitat-related pests that allows for broadcast coverage with a variety of solid or flowable protein-polysaccharide complex formulations with conventional application methods without significant losses to wind drift, while enhancing canopy penetration or target substrate adherence.

Another object of the present invention is the development of a controlled release plant protection agent in the form of preserving compositions containing foliar nutrients for cut flowers.

These and other objects are accomplished by the compositions and method of the present invention.

SUMMMARY OF THE INVENTION

The present invention relates to a solid or variable-viscosity flowable (i.e., sprayable, pumpable, injectable) plant protection agent delivery composition made from a protein-polysaccharide complex with or without water, and containing: one or more liquid and/or solid herbicides, desiccants, algicides, defoliants, hormones, plant growth regulators, plant growth inhibitors, foliar nutrients, petroleum oils or solvents, sterilants, biological control agents, microbial control agents and pesticidal agents, such as insecticides, mosquitocides, schistomacides, molluscicides, ovicides, larvicides, monomolecular films, duplex films, monolayers, petroleum oils, pupicides, biological control agents, pathogens, parasites, microbial control agents, insect growth regulators, conventional toxicants, pesticides, chemosterilants, surface-active agents or film-forming agents; with or without one or more nontoxic adjuvants or diluents such as carriers, binders, deflocculating agents, dispersing agents, penetrants, spreading agents, surface-active agents, surfactants, suspending agents, wetting agents, stabilizing agents, compatability agents, sticking agents, waxes, oils, inverting oils, co-solvents, coupling agents, foams, antifoaming agents, synthetic plastics, elastomers, synergists, natural or synthetic polymers; and other additives and mixtures thereof.

The present invention also relates to a facile method of applying the solid or flowable, aqueous-or oil-base, plant protection agent delivery composition with one or more active ingredients, to control, preserve or treat a variety of plants or related vegetation or to control a variety of insects in all types of environments with conventional ground or aerial techniques.

This invention further relates to a facile method of combining, mixing, encapsulating, agglomerating, or formulating herbicidal, insecticidal and foliar nutrient ingredients or mixtures thereof, optionally with water or oil, and/or various nontoxic adjuvants, diluents or carriers, etc., with a protein-polysaccharide complex into solid powders, dusts, granules, pellets, or briquets, and/or into flowable, variable-viscosity formulations such as solutions, dispersions, emulsions, sols or semi-gels. The use of a protein-polysaccharide complex in this manner makes possible the mixing or singular application of herbicidal, insecticidal and foliar nutrient ingredients or mixtures thereof with other additives that would otherwise be difficult to combine as flowable formulations.

In particular, the present invention is directed toward a method of formulating a protein-polysaccharide complex with plant protection agent including herbicidal agents, insecticidal ingredients and foliar nutrients or mixtures thereof, with or without water or other additives, into solid powders, dusts, granules, pellets or briquets, or into flowable, variable-viscosity solutions, dispersions, emulsions, sol or semigel-like preemergence or postemergence formulations that can produce quick, slow, controlled, prolonged, or extended release of one or more active ingredients to simultaneously or independently control or treat a variety of plants and insects.

The use of protein-polysaccharide complexes of the present invention provides simple and easy techniques for the incorporation or encapsulation of a variety of herbicidal agents, pesticidal agents and/or foliar nutrients into agglomerated or non-agglomerated solid carrier matrices, e.g., dense pellets, granules, or briquets, for the slow or controlled release of active agents in a variety of plant an pest habitats.

Agglomerated or non-agglomerated protein-polysaccharide complex formulations of the present invention containing one or more diluent or adjuvant surfactant(s), oil(s), surface-active agent(s) or film-forming agent(s), can effect a mechanism for reducing the rate of water absorption, and thereby slow down the rate of release of one or more active agent(s) from the solid matrices, and extend the field life or persistence of the active agent(s) for a period of time greater than would be expected with protein-polysaccharide complex formulations containing no surfactant(s), filim-forming agent(s), surface-active agent (s), or oil(s). Similarly, certain of the flowable, variable-viscosity protein-polysaccharide complex compositions of the present invention, which are formulated with water and/or one or more surfactant(s), oil(s), surface-active agent (s), or film-forming agent(s), can slow or control the release rate of the active formulation ingredients, while enhancing target substrate adherence and minimizing wind drift loss.

The solid or flowable compositions of protein-polysaccharide complex will also be suitable with various preemergence herbicidal agent(s), with or without additional pesticidal agent(s) or other additive(s) which can be directly incorporated on, and/or into, dry or moist soil by various techniques (e.g., soil injection). The protein-polysaccharide complex carrier/diluent/encapsulation matrix facilitates resistance to surface/subsurface run-off or percolation losses of the active agents. Varied applications from broadcast to point-specific, controlled-release applications against a variety of weeds can be accomplished by adjusting the agglomeration or formulation process, and/or the specific gravity of the carrier/matrix, and thereby produce formulations that can float and/or sink in an aqueous environment, or provide broadcast or point-specific coverage on land for controlled, quick or long-term release. For example, when a dense pellet is employed, the resulting sinking formulation can be evenly distributed over an aquatic environment without herbicidal loss or redistribution problems due to run-off or wind fetch. In addition, variable-viscosity, sprayable, pumpable, or injectable formulations of protein-polysaccharide complex and one or more surfactant(s), oil(s), surface-active agent(s) or film-forming agent(s), formulated with or without water, can effect a similar mechanism for variable time-release (i.e., slow or controlled release) of active ingredients in compositions, thereby extending the field life or persistence of the herbicide(s), with or without additional pesticidal additives, for a greater period of time than would be expected with protein-polysaccharide complex formulations containing no surfactant(s), oil(s), surface-active agent(s) or, film-forming agent(s). This can extend the field persistence of the active agent(s) in the flowable protein-polysaccharide complex formulation, and thereby assure that the frequency of costly herbicidal retreatments per habitat will be reduced.

The protein-polysaccharide complex (PPC) composition used as a binding or stabilizing compound or as a carrier in the present invention includes a water-soluble polysaccharide and a substantially water-insoluble protein. The protein-polysaccharide complex composition can be formed in granular form or as a solution.

The solid or flowable PPC formulations of the present invention may be composed of one or more of a wide choice of solid and/or liquid herbicidal agents, such as herbicides, algicides, desiccants, defoliants, hormones, plant growth regulators, plant growth inhibitors, petroleum oils or solvents, biological control agents, microbial control agents, pathogens, or parasites, with or without additional pesticidal agents ingredients, such as insecticides, mosquitocides, schistomacides, molluscicides, insect growth regulators, conventional toxicants, pesticides, chemosterilants, film-forming agents, monolayers, duplex films, monomolecular surface films, or petroleum oils, and with or without non-toxic agents such as water, surfactants, spreading agents, adjuvants, carriers, binders, deflocculating agents, dispersing agents, synergists, penetrants, suspending agents, surface-active agents, film-forming agents, sticking agents, wetting agents, stabilizing agents, compatibility agents, co-solvents, coupling agents, foams, anti-foaming agents, diluents, waxes, oils, synthetic plastics, elastomers, inverting oils, natural or artificial polymers, and other additives and mixtures thereof; depending on the type or nature of the plant or insect habitat to be controlled, the environmental impact, and/or the plant developmental stage and/or associated insect or pest species to be controlled. The solid or flowable formulations of the present invention are biodegradable. They are also storage stable when formulated, basically as stable as the individual components; however, increased stability may occur in solid matrix form over the flowable form. Solid or flowable PPC formulations of the present invention can take a wide variety of shapes, forms, and consistencies which may be required for a particular application. The solid or flowable PPC formulations of the present invention can have a variable time-release, either quick, or gradual as the situation requires. The present invention provides a PPC carrier, suspending, compatibility, formulating or encapsulation agent for the variable time-release or delivery of separate or joint-or multiple-active formulations of liquid and/or solid herbicidal and pesticidal agents that would otherwise be difficult or impossible to combine or mix as technical, oil-, or water-base products into a homogeneous solid or flowable formulation.

Solid or flowable, herbicidal containing PPC formulations of the present invention can be used to control preemergence or postemergence weeds or related vegetation in areas that are dry, moist, semi-aquatic or aquatic.

Compaction or agglomeration of the PPC matrix of the present invention has been shown to effect a slow or controlled release mechanism for certain active ingredients. Generally, compaction or agglomeration will occur subsequent to mixing/blending with the active agents and various adjuvants. However, water soluble active agents and emulsions can be diffused to the matrix prior to or subsequent to agglomeration, and then reagglomerated or compacted if desired.

Other objects, aspects and advantages of the present invention will be apparent to one of ordinary skill in the art from the following:

DESCRIPTION OF THE PREFERRED EMBODIMENTS

Protein-polysaccharide complexes constitute a novel class of chemicals useful as plant protection agent delivery compositions for controlling populations of plants or related vegetation and insects in an environment area needing plant and insect control or treatment. Plant protection agents within the concept of the present invention are understood to include herbicidal agents, insecticidal agents and foliar nutrients.

A plant protection agent delivery composition is any composition which can carry, or be adapted to carry a herbicidal agent, a pesticidal agent or a foliar nutrient, or mixtures thereof to the target habitat, natural or artificial, aquatic, semi-aquatic, moist, or dry. The plant protection agent delivery agent matrix for incorporation into solid or flowable compositions is a proteinpolysaccharide complex (PPC).

The protein-polysaccharide complex (PPC) composition used as a binding or stabilizing compound or as a carrier in the present invention includes a water-soluble polysaccharide and a substantially water-insoluble protein. The protein-polysaccharide complex composition can be formed in granular form or as a solution.

Examples of polysaccharides that can be used to prepare the PPC composition include, but are not limited to water-soluble cellulose derivatives, seaweed polysaccharides such as alginate and carrageenin, seed mucilaginous polysaccharides, complex plant exudate polysaccharides such as gum Arabic, tragacanth, guar gum, pectin, ghatti and the like, and microbially synthesized polysaccharides such as xanthan gum. In a preferred embodiment, the polysaccharides are guar gum, pectin, gum Arabic and mixtures thereof. The most preferred polysaccharide for use in the present binding or stabilization composition is guar gum.

The polysaccharide is present in the PPC composition in an amount ranging between about 90% to 99.5% by weight of the combined polysaccharide and protein components in the PPC composition, preferably in an amount ranging between about 95% to 99% by weight of the combined polysaccharide and protein components of the PPC composition.

Similarly, proteins useful in the binding or stabilizing PPC composition can be any protein that is predominately or substantially water-insoluble, however, vegetable proteins or prolamines are advantageously preferable due to their availability. Prolamine is a cereal-derived protein that is insoluble in water, absolute alcohol or neutral solvents and soluble in dilute (80%) alcohol. Examples of suitable prolamines for use in the present invention include, but are not limited to, corn-derived prolamine or zein, barley-derived prolamine or hordein, and wheatderived prolamine or gliadin.

In a preferred embodiment of the invention, the vegetable protein or prolamine used in the composition is zein or corn gluten. Zein is extracted from corn or maize. PPC compositions containing zein are used to form odorless, clear, hard and almost invisible films. Sixteen amino acids have been isolated from zein including glutamic acid or glutamine, leucine, proline, alanine, phenylalanine, isoleucine, serine, tyrosine and asparagine. The remaining seven amino acids are present in amounts of less than 3% by weight.

Zein is commonly extracted from corn gluten by physical separation means as opposed to chemical separation means. Whole corn zein contains a heterogeneous mixture of disulfide linked aggregates. Commercial extraction of zein generally results in a product with a molecular weight of about 25,000 to 35,000. Zein contains a high proportion of hydrocarbon group side chains and has a high percentage of amide groups present with a relatively low amount of free carboxylic acid groups.

The substantially water-insoluble protein is present in the PPC composition in an amount ranging between about 0.5% to 10% by weight of the combined polysaccharide and protein components of the PPC composition, preferably in an amount ranging between about 1% to 5% by weight.

Relatively small amounts of a pH adjusting compound in the form of an acid or an acidulant are preferably used to lower the pH of the aqueous polysaccharide solutions during preparation of the PPC compositions to between 1 to 11.5, preferably about 3.8 to 8.5. The acidulants enhance the water dispersibility of the PPC compositions, thereby facilitating reconstitution of the protein-polysaccharide complex compositions in water. Although any pH adjusting acidic compound is useful in the present invention, including inorganic acids such as carbonic acid, sulfuric acid, hydrochloride acid and the like, it is preferable to utilize organic acids, preferably $C_1$ to $C_{20}$ organic acids. Suitable organic acidulants include, but are not limited to, citric acid, malic acid, adipic acid, tannic acid, lactic acid, ascorbic acid, acetic acid, fumaric acid and the like and mixtures thereof. In a preferred embodiment, citric acid is used.

The acids or acidulants are preferably used in an amount between about 0.25% to 5% by weight of the combined weight of polysaccharide and protein components of the PPC compositions, preferably in an amount between about 0.5% to 1% by weight. The acid is preferably added to the water of an aqueous organic solvent system prior to addition of the protein and polysaccharide organic component.

PPC compositions are preferably prepared by dissolving a water-insoluble protein or prolamine in an aqueous organic solvent system containing the pH adjusting acidic component to form a protein solution. A soluble polysaccharide is then added to the protein solution to form a protein-polysaccharide complex in solution. If desired, the solvent is then separated or evaporated from the solution to yield the final protein polysaccharide complex composition.

The aqueous organic solvent system is a mixture containing at least one organic solvent in water. Suitable organic solvents include, but are not limited to, alcohols such as ethyl alcohol and isopropyl alcohol; glycols such as propylene glycol and polyethylene glycols; and, ketones such as acetone. In a preferred embodiment of the invention, the aqueous organic solvent system is either aqueous ethyl alcohol or aqueous isopropyl alcohol. Alcohols generally can hold up to six grams of zein in solution for each 100 milliliters of alcohol.

The desired ratio of water to organic solvent in the aqueous organic solvent system is dependent on factors such as the miscibility of the solvent in the water and the amount of protein to be dissolved. When the organic solvent system is aqueous ethyl alcohol or aqueous isopropyl alcohol, the amount of water generally ranges between about 10% to 40% by weight and the amount of alcohol generally ranges between about 60% to 90% by weight. More preferably, the amount of water in such systems is between about 25% to 35% and the amount of alcohol is between about 65% to 75%.

The substantially water-insoluble protein or prolamine is added to the aqueous organic solvent system in an amount between about 100 and 300 grams of prolamine per liter of aqueous organic solvent system, more preferably in an amount between about 120 to 240 grams per liter. The dissolution is carried out at a temperature between about 20° C. (ambient room temperature) and about 60° C., preferably about 30° C. using conventional agitation methods to form a protein solution. Soluble polysaccharide in minute fiber or particulate form is then admixed with the protein solution to form a PPC in solution.

In an alternative embodiment, a protein containing gluten such as corn gluten can be directly added into the aqueous organic solvent system instead of pure zein. In this preparation procedure, the zein protein portion of the gluten passes into solution while the deprotenated nonzein remainder of the gluten can be separated by vacuum filtering or other standard separation techniques. An incidental amount of up to 100% by weight of expended or deprotenated gluten can be present in the recovered admixture with the protein-polysaccharide complex without adversely affecting the properties of the PPC, however it is preferable to employ amounts up to 10% by weight of the gluten.

The protein-polysaccharide portion of a PPC in solution generally contains between about 90% to 99.5% by weight of polysaccharide, between about 0.5% to 10% of a protein. The PPC solution preferably additionally, contains between about 0.25 to 5% by weight of a pH adjusting component based upon the total weight of protein and polysaccharide. More preferably, the PPC solution contains between about 95% to 99% of polysaccharide and between about 1% to 5% of vegetable protein based on the total weight of polysaccharide and protein.

It is important that the substantially water-insoluble protein or prolamine thoroughly impregnate the soluble polysaccharide particles during the process of admixing the soluble polysaccharide with the protein solution. The aqueous organic solvent system used to prepare the protein solution should wet the soluble polysaccharide particles so that the hydrophilic soluble polysaccharide particles are impregnated or coated with the hydrophobic protein to form the PPC in solution.

The mixing process to prepare PPC in solution is carried out until a complete uniform mixture is attained. In general, the process is carried out at a temperature between about 20° C. and 60° C., preferably between about 20° C. and 25° C. for a time period of between about 10 and about 30 minutes, preferably between about 10 and 15 minutes. The PPC in solution is agitated during the mixing process by conventional agitation methods including, but not limited to, manual shaking, mechanical shaking, magnetic stirring, mechanical stirring or a combination thereof.

Additives that promote impregnation may be added at any point during the admixing process. Suitable additives include, but are not limited to, detergents and emulsifiers. Exemplary additives are polysorbates, oils and albumin. Additives may be used in an amount between about 0.25% to 5.0% by volume of the PPC in solution, preferably between about 0.5% to 1.0%.

Once the PPC in solution has been prepared, the solvent is optionally separated or evaporated to yield a protein-polysaccharide complex composition, that is, a particulate polysaccharide impregnated or complexed with a protein. Any number of solvent removal techniques may be used including, but not limited to, vacuum drying, centrifugation, evaporation, freeze drying, air drying, convection oven drying or a combination thereof. One preferred method of extracting the solvent is vacuum drying which safety removes and recovers the solvent while drying the product to provide the PPC composition. The proteinpolysaccharide complex composition provided in accordance with the invention can be further processed by grinding or milling to a desired mesh particle size for use as a powder and the like. The PPC of the present invention are typically in an powder, granule, or flake form, adapted to be blended and/or agglomerated with the herbicidal/pesticidal agent.

In another embodiment, the PPC in solution can be mixed directly into water for admixture with the plant protection agent compositions. The PPC solution can be diluted with water for administration into the herbicidal and/or insecticidal compositions. Typically an aqueous solution of PPC contains 0.1 to 50 grams of PPC per liter of water.

Specifically, it has been found that when the PPC of the present invention is impregnated or mixed with a surface-active agent, film-forming agent or oil, water will be absorbed at a slower rate, so that active agents in the solid matrix or flowable matrix formulations will be differentially released at slower rates than would be expected with formulations containing no surfactants, etc. This also acts as a restraint on the hydrodynamic activity of the formulation when activated, allowing for deactivation and subsequent reactivation depending on environmental factors.

A herbicidal agent is any chemical, agent, or mixtures of chemicals and/or agents used for killing or controlling immature or mature stages of plants (weeds), or for severely interrupting their normal growth processes. Herbicidal materials may effect preemergence or postemergence vegetation and can include herbicides, desiccants, algicides, defoliants, hormones, plant growth regulators, plant growth inhibitors, petroleum oils or solvents, sterilants, biological control agents, microbial control agents, pathogens and/or parasites. Conventional herbicidal agents and formulations therefor that may find application in the present solid or flowable, herbicidal delivery compositions include Acrolein, Amitrole, Ammonium Sulfamate, Bromacil, Copper/Copper Sulfate, Dalapon, Dicamba, Dichlobenil, Diquat, Diuron, Endothall, Fenac, Fluridone, Glyphosate, Petroleum Solvents, Picloram, Prometon, Silvex, Simazine, Tebuthiuron, Trichloroacetic Acid, 2,4-D, Velpar, Xylene, Aquazine.RTM., Aquathol K.RTM., Aquashade.RTM., Aqualin.RTM., Banvel.RTM., Casoron.RTM., Cutrine.RTM.-Plus, Cytrol.RTM., Amitrole.RTM.-T, Dichlone.RTM., Dowpon.RTM., Endothal.RTM., Fenac.RTM., Hydrothal.RTM.-191, Hydrothal.RTM.-47, Hydout.RTM., K-Tea.RTM., Komeen.RTM., Karmex.RTM., Monuron.RTM., Revenge.RTM., Rodeo.RTM., Roundup.RTM., Scout.RTM., Sonar.RTM., Spike.RTM., System E.RTM., System L.RTM., Banvel.RTM.-720, Aqualine.RTM., Ammate.RTM., Hyvar.RTM., Cardi.RTM., Tordon.RTM., 22K, Primatol.RTM., Pramitol.RTM., Juron.RTM., Aqua Kleen.RTM., Weedone.RTM., Velpar.RTM., Diquat.RTM., and others and mixtures thereof. These herbicides and herbicidal formulations, the plants that they control, effective application rates, and the like are discussed by W. T. Thomson, 1986, in Agricultural Chemicals, Book II Herbicides, 1986–87 Revision, Thomson Publications Fresno Calif. 301 pp. and by Dr. Edward 0. Gangstad, 1986, in Freshwater Vegetation Management, Thomas Publications, Fresno, Calif., 380 pp. Film-forming agents, surface-active agents, surfactants, or oils, useful in solid or flowable formulations of the present invention as carriers, diluents, adjuvants, release rate modifiers, insecticides, pesticides, etc., are generally organic chemicals that are soluble to essentially insoluble in water. They are nonionic, anionic, or cationic, generally nonvolatile, and can be liquid, semisolid, or solid. They may have a low freezing point and a boiling point above the maximum air temperature of the environment into which they are placed.

Examples of liquid, semisolid, or solid film-forming or surface-active agents useful in conjunction with the present invention for herbicidal, pesticidal or foliar nutrient purposes are: the organic chemicals described in U.S. Pat. No. 4,160,033, which is herein incorporated by reference; and organic chemicals that reduce the water surface tension to greater than 31 dynes/cm and/or have an HLB No. greater than 10. HLB stands for "Hydrophile-Lipophile Balance," as define in THE ATLAS HLB SYSTEM, Atlas Chemical industries, Inc. (4th printing), 1963. The HLB number is an indication of the percentage of the hydrophilic portion of the nonionic emulsifier molecule, as defined on pages 3 and 18 of this reference.

Film-forming or surface-active agents such as 2-propanol, tridecyl alcohol, 2-ethyl butanol, 2-ethyl hexanol, 1-hexanol, acetone, xylene, decyl alcohol, polyoxyethylene (20) sorbitan trioleate, polyoxyethylene alkyl aryl ether, polyoxyethylene (5) sorbitan monooleate, isostearyl alcohol containing 10 oxyethylene groups, Morwet.RTM. surfactants, isostearyl alcohol containing 20 oxyethylene groups; cetyl alcohol; stearyl alcohol; or surface-active, petroleum-base oils such as mineral oils, diesel oils, etc., and mixtures thereof may be used.

Various other exemplary surfactants include higher fatty acids, higher alcohol sulfate, alkyl aryl sulfonates, polyoxyethylene sorbitan alkyl ether, polyoxyethylene alkyl phenol ether, polyoxyethylene sorbitan alkyl ester, polyoxyethylene alkylamine, polyoxyethylene aklylamide, poly(oxyethylene-oxypropylene) co-polymer and polyoxyethylene-polyoxypropylene alkylene diamine alkyl trimethyl ammonium salt, alkyl dimethyl benzylammonium salt, alkylpryidinium salt, alkyl betaine or alkylimidazoline sulfonate.

A pesticidal agent is any substance or mixture of agents and/or substances used to control or kill adult or immature stages of insects (particularly mosquitoes), snails, or other pests or organisms (i.e. cercaria, miracidia) that breed in dry, semi-dry or wetland habitats. Exemplary pesticidal materials can include insecticides, pesticides, molluscicides, schistomacicides, ovicides, larvicides, pupicides, adulticides, biological control agents, microbial control agents, pathogens, parasites, insect growth regulators, conventional toxicants, chemosterilants, film-forming agents, monolayers, monomolecular surface films, surface-active agents, duplex films, petroleum oils or vegetable oils. Pupicides, larvicides, and insect growth regulators for the control of immature mosquitoes are of specific interest. Pesticidal agents (i.e., insecticides, pupicides, larvicides, insect growth regulators, pathogens, etc.) useful in the present invention are discussed in W. T. Thomas, 1985, Agricultural Chemicals, Book 1 Insecticides, 1985–86 Revision, Thomas Publications, Fresno, Calif., pp. 1–255, and in George 0. Poinar, Jr. and Gerald M. Thomas, 1978, Diagnostic Manual for the Identification of Insect Pathogens, Plenum Press, N.Y., pp. 1–218. Exemplary pesticides are selected from the group comprising insecticides, nematocides, fungicides and herbicides; and possibly molluscicides and rodenticides. More particularly, the active ingredient may be selected from the group comprising organophosphate, carbamate, benzimidazole, dicarboxamides, bipyridols, pyrethroids and chlorinated hydrocarbons. Typical examples are azinphos methyl, benomyl, captan, dimethoate, ethyl parathion, methomyl, trichlorfon, oxamyl, dibrom, dimecron, mevinphos, monocrotophos, paraquat, diquat, cypermethrin and dicofol. Of these, azinphos methyl, dimethoate, ethyl parathion, trichlorfon, dibrom, dimecron, mevinphos and monocrotophos are organophosphate; methomyl and oxamyl are carbamate; benomyl is a benzimidazole; captan is a dicarboxamide; paraquat and diquat are bipyridols; cypermethrin is a pyrethroid; and dicofol is a chlorinated hydrocarbon.

A pupicide is any material that can kill that specific developmental stage of certain aquatic insects called a pupa. Pupicides are usually chemicals that kill pupae directly by forming petroleum or non-petroleum films on the surface of water that cause the pupae to drown. This stage is nonfeeding and directly precedes the adult stage. Examples of pupicides useful in accordance with the present invention is Arosurf.RTM. MSF or other film-forming agents described in U.S. Pat. No. 4,160,033, and petroleum oils such as FLIT MLO.RTM., GB-111 or GB-1356. Biological/microbial pupae control agents such as bacteria, fungi, protozoa, viruses, rickettsiae or nematodes may also be used at a future time.

A larvicide is any material that can kill that specific developmental stage of certain aquatic insects called a larva. Larvicides can kill larvae after ingestion of a toxic material, kill on or after contact with the integument, or kill by physical (nontoxic) and/or toxic means by causing the larvae to drown. The larval stage is a feeding stage that usually has several molting or growth phases called instars. For example, in mosquitoes there are four larval instars. The larval stage directly precedes the pupal stage. Examples of larvicides useful in accordance with the present invention include biological control agents or microbial control agents such as Bacillus thuringiensis var. israelensis (e.g., Vectobac.RTM., Bactimos.RTM., teknar.RTM., Skeetal.RTM., Mosquito Attack.RTM.) or Bacillus sphaericus (e.g., BSP-1); conventional toxicants such as Abate.RTM., Baytex.RTM., Dursban.RTM., Prentox.RTM., Pyrenone.RTM., resmethrin, malathion, pyrethrins, allethrin, Baygon.RTM., Furadan.RTM., methoxychlor, etc; nonpetroleum film-forming oils such as Arosurf.RTM. MSF; and petroleum oils such as FLIT MLO.RTM., GB-111, and GB-1356. Fungi (such as Lagenidum giganteum, mycelia and oospores), protozoa, viruses, rickettsiae and nematodes may also be used.

Insect growth regulators (IGRs) are chemicals such as juvenile hormone or anti-juvenile hormone analogues that kill the target aquatic environment insect in one or more immature stages by adversely affecting the molting or developmental cycle. IGRs are not considered to be direct larvicides or pupicides. For the most part, larvae that are exposed to the chemical continue to develop normally until they reach the pupal stage where they die. Examples of IGRs are Altosid.RTM., Dimilin.RTM., and fenoxycarb (Pictyl.RTM.).

Foliar nutrients useful in the formulations of the present invention are useful as preemergent and postemergent fertilizers for all types of crops, flowers, plants and trees including but are not limited to: nitrogenous fertilizers, phosphate fertilizers, potassium fertilizers or mixtures thereof. Examples of nitrogenous fertilizers are ammonium sulfate, calcium ammonium nitrate, urea, urea aldehyde condensates, magnesium nitride ammonium sulfate/nitrate (the mixture), calcium nitrate and calcium cyanamide. Examples of phosphate fertilizers are superphosphate, double superphosphate, triple superphosphate, ground basic slag, basic (Thomas) steel process phosphate, calcined phosphate, "rhenania phosphate" (phosphate product containing rhenanite), dicalcium phosphate and rock phosphate. Examples of potassium fertilizers are potassium chloride, potassium sulfate and potassium magnesia. Further examples of principal nutrients are calcium carbonate, such as limestone or chalk; calcium oxide; magnesium oxide; kieserite and dolomite. Organic components may also be mixed in: guano, fish meal, bone meal, lignin or peat. Trace elements, i.e., micronutrients, include manganese, zinc, iron and copper, e.g., zinc oxides, zinc sulfates, zinc carbonates, copper oxides, molybdenum sulfates and borates.

When fertilizers are combined with the protein-polysaccharide complex composition to form the controlled release plant protection agent delivery composition of the present invention, this delivery composition is useful to fertilize all types of crops, flowers, plants and trees in a controlled release manner over long periods of time, often up to two years or more with a single application of the controlled release plant protection agent delivery composition. This composition is also useful as an additive to water to preserve or extend the life of cut flowers. An aqueos solution of controlled release plant protection agent delivery composition containing PPC and a foliar nutrient or fertilizer is useful in increasing the durability of cut flowers and has a broad spectrum of effectiveness in regard to the various, particularly commercially available flower species. They are, for example, suited for chrysanthemums, roses, carnations, irises, gerbera, calendula, gladioluses, lilies, and so on. The present method of preserving cut flowers is performed by forming an aqueous solution containing at least one protein-polysaccharide complex composition comprising: between about 90% to 99.5% by weight of a water-soluble polysaccharide impregnated with between about 10% to 0.5% by weight of a substantially waterinsoluble protein; and at least one foliar nutrient, and inserting the cut flowers therein. The foliar nutrient are present in a total amount effective to preserve a target population of cut flowers, typically from 0.5 to 5 weight percent of the solution. Cut flowers thus treated have a preservation coating formed upon their stems to further preserve the cut flowers upon transportation under non-aqueous conditions such as the shipping of roses or orchids in boxes.

Nontoxic adjuvant or diluent materials include water, carriers, binders, deflocculating agents, penetrants, spreading agents, surface-active agents, surfactants, suspending agents, wetting agents, stabilizing agents, compatibility agents, waxes, oils, inverting oils, co-solvents, coupling agents, foams, synergists, anti-foaming agents, synthetic plastics, elastomers, natural or synthetic polymers, and other additives and mixtures thereof.

Plants (weeds) and related vegetation that can be treated with the herbicide of the present invention are any vegetation that is treatable with the particular herbicide selected for use including but are not limited to tan oak tree, mandrose, crabgrass, algae, floating plants, emersed plants, submersed plants, shore, irrigation, and ditch bank plants, and marginal plants or sedges, grasses, and rushes.

The PPC/pesticide formulations of the present invention can be directly applied via solution or in solid form onto animals or physical objects such as rugs, furniture and the like to eliminate pests which have infested these animals or objects.

Flowable formulations are made by the addition of water or water-based plant protection agents containing formulations to various concentrations of PPC or vice versa, thereby producing flowable (e.g., sprayable) PPC aqueous formulations that have the desired plant protection agent and viscosity. Viscosity modification will mainly be a function of the active and/or inactive formulation components. Therefore, the viscosity of the formulations can be altered to achieve optimum flow ability, droplet size and quantity, and thereby improve the general ground or aerial application characteristics of the formulation for maximum control of the target plant or pest.

Furthermore, active pesticidal ingredients encapsulated in the viscous/semi-viscous, flowable, aqueous PPC formulation can be protected from degradation from the effects of ultraviolet radiation, volatilization, temperature, microbial activity, evaporation, run-off, etc., particularly when used in preemergence/pretreatment habitats. Furthermore, evaporation of water from the flowable formulation can result in a solid congealed-like pesticide encapsulated matrix, thereby protection the active components for prolonged periods until release of the active ingredient(s) is triggered when the habitat is flooded with water.

As briefly discussed above, impregnation or mixing of PPC with fatty alcohols, film-forming agents, surface-active agents, surfactants, or hydrophobic oils appears to delay or slow down the rate of water absorption of PPC, thereby providing a useful mechanism for affecting slow or controlled release of nutrients, herbicidal agents or pesticidal agents from non-agglomerated or agglomerated formulations. These agents can be simply incorporated into the non-agglomerated or agglomerated PPC matrix by mixing and subsequent temperature or moisture treatment, thereby entrapping the hydrophobic agent into a matrix. The slow or controlled release process could be further modified or delayed by varying the concentration of adjuvants or diluents such as film-forming agent(s), surface-active agent(s), surfactant(s), or oil(s), and by adding one or more binders.

When the present formulation is used in contact with water, the water is differentially held within the variable-viscosity PPC matrix at a strength that is dependent on whether a solid or flowable formulation is used (i.e., the amount of water in the formulation), and therefore evaporates slower than an equivalent amount PPC-free standing water. Furthermore, the addition of film-forming agents, surface-active agents, surfactants, or oils to the PPC formulation also appears to retard the rate of water loss.

Any suitable equipment or technique used to incorporate the plant protection agents into an aqueous emulsion can be suitably used to mix these additives into the PPC formulation. Inverting oil techniques are also appropriate for mixing and dispensing a highly viscous aqueous PPC composition composed of water, at least one plant protection agent, film-forming agent or oil, with or without other additives.

The specific gravity of the delivery composition can be adjusted by the use of solid or liquid surfactants, oils, surface-active or film-forming agents, alcohols, clays, taics, fillers which can include viscosity modifiers and the like.

The water or surfactant, surface-active agent, film-forming agent, or oil-dissolved, oilsuspended, or oil-dispersed active and inactive agents can be incorporated into the PPC formulation as an emulsion. Suitable emulsifying agents can be used to form a stable emulsion, however, an unstable emulsion may be preferred for certain applications. Suitable emulsifiers include those disclosed in U.S. Pat. No. 4,606,773 or any conventional emulsifier such as ammonium lineolate, ethylene oxide adducts, acyl polyglycol ethers, oxyethylated fatty alcohols, alkali metal starches as discussed in U.S. Pat. No. 2,347,680, or starch propionates as disclosed in U.S. Pat. No. 4,059,458. However, any suitable known surfactant, surface-active agent, film-forming agent, or oil can be employed.

The amount of active agent in the delivery composition will depend on the target plants or related vegetation or insect population, the active nutrient, herbicidal or pesticidal agent involved, the amount of PPC in the formulation, whether or not water is present, adjuvants and/or diluents are added. All amounts of the active agents are incorporated in application rate amounts known to be effective to persons skilled in the art. Generally, the weight ratio of PPC composition to foliar nutrient, herbicidal agent and/or any pesticidal is from about 0.1:100 to about 100:0.001, the foliar nutrient, herbicidal and/or the pesticidal agent being incorporated in the solid or flowable delivery composition for application at rates at or below those rates effective to control the target plant or pest or to preserve cut flowers as are known to those skilled in the art. The ratio of PPC to any additive diluent or adjuvant such as a surfactant, oil, surface-active agent or film-forming agent is from about 0.1:1 to about 100:1. The ratio of PPC to water in a flowable composition is generally 0.001:100 to 1:20.

EXAMPLE A

A 10% zein solution was prepared by dissolving 10 grams of unstripped zein in 90 grams of an aqueous isopropyl alcohol solution. The aqueous isopropyl alcohol solution contained 15% water by weight and 85% isopropyl alcohol by weight. Dissolution was carried out in a 500 ml beaker and the solution was initially stirred using a mechanical stirrer at a speed of over 100 rpm in order to fully wet the zein. Once all of the zein was dispersed, the stirring speed was reduced by about ½ for an additional five minutes to insure complete dissolution of the zein in the aqueous isopropyl alcohol solution and to produce a protein solution. The ambient temperature was maintained at 22° C. throughout this procedure.

Two hundred grams of milled guar gum powder (fine-60 mesh, TIC GUMS, Belcamp, MD) was slowly added to the protein solution with vigorous stirring using a mechanical stirrer at a speed of over 100 rpm. Manual stirring was started as the mixture thickened. Additional aqueous isopropyl alcohol was added to attain a soupy appearance indicative of successful impregnation of the soluble guar gum particles by the zein solution. Agitation of this soupy liquid mixture was maintained for fifteen minutes. The resulting PPC solution was dried under reduced pressure of 0.05 atmospheres. at a temperature of 60° C. using a lab-line Duo-Vac vacuum oven manufactured by LabLine Corp., Melrose Park, Ill. The resulting recovered dried PPC composition was a yellowish-beige color and was milled to a granular form (80 mesh).

In the following examples the PPC used to formulate insecticide and herbicide compositions was prepared in accordance with the procedure of Example A and unless otherwise indicated all percentage are percent by weight.

EXAMPLE 1

An insecticide solution was prepared in 1000 ml of an aqueous alcohol solution containing 85 % of ethyl alcohol and 15 % of water by mixing 5% Methoxychlor, 3.9% Malathion, 5% Captan and 86.1% PPC and stirring the ingredients at 500 RPM's for 15 minutes in a glass beaker. The resultant solution was then dried by vacuum and recovered by further drying into a cake and ground into a 200 screen powder.

Ten grams of the recovered screen powder was later added to 4000 mls of water and mixed until fully dissolved. The contents were placed into a portable agricultural spray device and the insecticide was onto an apple tree infested with aphids. The tree was inspected 24 hours later and all of the aphids were dead. Another second inspection one week later showed that no new colonies of aphids had infested treated tree.

EXAMPLE 2

To 1000 ml of an aqueous alcohol blend containing 70 % of isopropanol and 30 % of water were added 0.02% Pyrethrins (0.09 grams), 0.13% Rotenone (0.585 grams) and 99.85% PPC (449.325 grams) and mixed for 45 minutes in an air driven mixer. The resulting mixture was then allowed to dry slowly at 98° F. The material was then ground into a fine powder and blended with 0.35 grams of DK ester F 160 Manufactured by Montello, Tulsa, Okla. 74135, as a wetting agent. Ten grams of the dry powder was mixed with 4000 ml of water in a magnetic blender for thirty minutes and poured into a small household plant sprayer (spraying device).

Six household plants infested with Alerodidae (White fly) were sprayed. Twenty-four hours later there was no evidence of either the winged adults larvae. When the newly infested but untreated plants were placed among the treated house hold plants no reinfestation of the PPC treated plants occurred over a one week period of time.

EXAMPLE 3

Twenty grams of caffeine (Hydrous Gran Alpha— Manufactured by BSAF, 4 Cranberry Rd., Parsippany, N. J. 07054) were dissolved into 120 mls of water maintained at a temperature of 80° C. To this solution 20 grams of PPC were added slowly. The mixture was allowed to cool and the water was removed by heating in an oven overnight. The resulting recovered cake was then ground to a screen size of 200 mesh. Five grams of the powder was blended into 4000 mls of water for 30 minutes until the mixture was fully wetted.

Twenty mls of the aqueous caffeine/PPCsolution was placed into a jar containing 50 mosquitoes. Twenty mls of rain water was placed into a separate jar containing the same number of mosquitoes. It was noted that the mosquitoes that came in contact with the VPP/caffeine solution became disoriented and could not feed when a hand was thrust into the jar. The mosquitoes that came into contact with the rain water fed normally.

Ten grams of the PPC/caffeine powder were blended with 4,000 mls of water for 30 minutes. The mixture was decanted into an agricultural spraying device. A grassy area containing a large number of active mosquitoes was sprayed with the mixture. The area was revisited in intervals of 30 minutes for two hours. On the first visit only ten mosquitoes were captured while feeding. On the second, third, and fourth no mosquitoes were captured. The site was visited on the second day after a light rain fall and only two mosquitoes were captured during a thirty minute period.

EXAMPLE 4

To 1000 ml of an aqueous alcohol solution containing 70% of isopropyl alcohol and 30% of water were added 10% Methoxychlor (20 grams) and 90% PPC (180 grams). The mixture was stirred for twenty minutes in an air driven mixer. The mixture was allowed to dry for 28 hours and then was ground into fine powder. Ten grams of the powder were dissolved in 4,000 mls of water containing 1 gram of a dry mix of an anionic-nonionic surfactant containing sodium lauryl trioxy ethylene, amine oxide and urea prill.

Three goats that were infested with Ectaparasites were washed with the mixture, rinsed and dried. After careful examination there was no evidence of infestation after the treatment.

EXAMPLE 5

Into 2000 ml of an aqueous alcohol solution containing 1% of isopropyl alcohol and 99% of water, were added a blend of 50% PPC (11 grams) and 50% Arylam (11 grams). The ingredients were blended for 30 minutes using an air driven blender. More of the aqueous alcohol solution was added to facilitate the mixing.

When the mixture was fully blended it was allowed to dry for 48 hours and then was ground into a fine powder. Twenty grams of the powder was "dusted" onto two rose bushes that were being defoliated by Japanese beetles. After one hour the beetles were killed off. The rose bushes were revisited after a rain shower and showed no signs of Japanese beetles. However, the untreated rose bushes along side the treated section were being defoliated by large numbers of Japanese beetles.

EXAMPLE 6

A charge of 100 grams of PPC was mixed into a glass beaker containing 200 mls of kerosene and 100 mls of water by an air driven mixer for 10 minutes. The liquid in the mixture was removed by vacuum drying. The remaining moist contents were then blended in the following ratio to make a paste: 5% Ronnel (5 grams), 1% Anionic/nonionic surfactant (1 gram), 94% Kerosene treated PPC (94 grams). Ten grams of the paste were mixed with 2,000 mls of water and scrubbed onto a floor infested with roaches. The roaches present during the scrubbing died. No roaches returned to the floor over a 30 day period of time.

EXAMPLE 7

A dry mix containing 4.23% disodium methanearsonate (4.23 grams) and 95.77% PPC (95.77 grams) was prepared by blending by tumbling for 30 minutes. The resulting powder was ground to a screen size of 100. To this powder 1 gram of DK ester F-1 60 Surfactant (Manufactured by Montello, 6106 East 32nd Place, Suite 100, Tulsa, Okla.) was added and hand mixed into the PPC blend. Ten grams of the dry powder were mixed into 4,000 mls of water for 20 minutes by an air driven blender. The mixed contents were decanted into a household sprayer and sprayed onto a twelve foot square section of lawn containing crab grass. The sprayed plot was examined twice at four weeks and four months. On both visits, no crab grass was observed. One year later the same plot was viewed again and there was no crab grass present.

EXAMPLE 8

A liquid herbicide was prepared by blending: 50 grams of ascorbic acid, 50 grams of citric acid, 10 grams of PPC and 4,000 mls of water. The liquid was hand stirred until all of the ingredients were fully dissolved. The contents were then decanted into a forestry sprayer. The herbicide was applied to the leaves of a variety of tan oak and madrone trees over an $\frac{1}{8}$th acre site. When the site was revisited one week later, the tan oak and madrone had suffered sever damage to their leaves but there was no apparent harm done to the naturally occurring nearby wild plants nor was there damage to the Douglas fir trees that had been planted on the site one year earlier. Twelve months later the test site was revisited. Both tan oak and madrone species that had been sprayed with the PPC/ herbicide were visibly dead. No new emerging growth of either tan oak or madrone was observed. There was no damage to the Douglas fir plantation nor to the wild grasses and flowers surrounding the killed tan oak and madrone trees.

It was noted that at the same time, the test site was being treated with the PPC/ herbicide solution a similar section of the Douglas fir plantation one quarter of a mile away was being sprayed with the herbicide Round Up. The Round UP site was visited in conjunction with the PPC/herbicide treated site. One week after Round Up was sprayed on the tan oak and madrone the leaves turned brown and appeared lifeless.

Twelve months later the same area had revegetated and the Round Up tan oak and madrone sprayed trees looked quite vigorous. A new application of Round Up had to be applied to prevent the leaves from blocking out the sun necessary to support the Douglas fir plantation.

EXAMPLE 9

Ten grams of PPC was added into 4,000 ml of water containing 8 grams of Ammonium Sulfamate. After mixing the solution in an air driven blender for 30 minutes, the liquid was poured into a conventional forestry sprayer.

A two hundred foot by two hundred foot section next to the Watson Pond Road, in Rome, Me. was sprayed with the solution and then revisited nine times over a period of twelve months. After six weeks it was apparent that the treated area had shown the effects of the spray application. Growth of mixed weeds had been halted. No further grooming was needed on the test site that year. The following year no grooming was needed on the site of the original application.

EXAMPLE 10

A herbicide/insecticide combination was prepared using 50 grams of citric acid, 50 grams of ascorbic acid, 20 grams of caffeine (anhydrous gran alpha) and 15 grams of PPC to 4,000 ml. of water. The ingredients were hand mixed in water until the blend was fully wetted. Two sites were chosen on Mohegan Island, Maine that contained similar stands of barberry bushes surrounded by native wild flowers and grasses. Both sites were adjacent to small marshy areas containing high mosquito populations.

Site A was sprayed with the PPC herbicide/insecticide blend. Within ten minutes after the PPC treatment, there were no active mosquitoes present. When site A was revisited 12 hours later, no mosquitoes were present. The barberry plant leaves were showing signs of withering. Site A was visited on week later and the barberry bushes were dying. It was also observed that the native grasses and wild flowers had remained vigorous and appeared to be untouched by the PPC spray. Mosquitoes were not a problem.

Twelve months later site A was revisited. The barberry bushes were completely dead. The grasses and wild flowers growth were not at all effected and no regrowth of barberry or new barberry plants on the site were observed.

Site B was sprayed with Round Up to kill the barberry bushes. Site B was difficult to work in because of the high concentration of mosquitoes not only during the spraying as well as during the visits to the site one week later and again in twelve months. On all visits to the site, it was necessary to wear long sleeved garments and head protection. When the site was visited twelve hours after spraying, a simple observation revealed that the Round Up was effective in defoliating the leaves of the barberry, but it had also damaged the native grass and was killing the wild flowers. One week later when site B was revisited, the barberry leaves had turned dry and had become discolored. The surrounding grass and wild flowers had turned brown. Twelve months later site B was visited again. Though there was still evidence of dead leaves on the barberry bushes, the plants had regained their vigor and had sprouted new leaves. Two new barberry plants were discovered on the site. The surrounding wild flowers and grasses were sparse and those present on the site were stunted. Erosion on the site was noted.

EXAMPLE 11

An aqueous solution was prepared in the following weight ratio: 1% PPC, 10% urea prill, 5,000 grams (CAS No. 57-13-6, Sohio chemical Company, Cleveland, Ohio), and 89% water.

The solution was stirred in a large tank for 45 minutes until all of the ingredients had dissolved. The solution was then sprayed onto a half acre lot in Rome, Maine having a surface area composed of ¾inch compacted highway aggregate mix. One hour after the solution had been placed on the aggregate, the area was planted by hand using USDA conservation grass mix. The area was then treated again with water only Andre-sprayed with water each morning for three weeks.

At the end of three weeks, the PPC/urea test site showed complete and uniform coverage of healthy mixed grasses. Normal watering conducted to maintain the lawn. Three seasons of healthy regrowth were observed with no further addition of the solution.

A similar plot directly adjoining the test site failed when conventional lawn fertilizers were used. Over a three year period, only small segments showed sparse growth of mixed weeds indicative of barren land.

EXAMPLE 12

An aqueous solution of a fertilizer composition (40,000 ml) was prepared by mixing by weight 5% citric acid, 5% ascorbic acid, 1% PPC and 89% water. An equal amount of the composition was sprayed onto two sites: Site A was a one acre tract of land north of Arcata, California managed by a lumber company and planted with Douglas Fir. Each tree was 12 inch height and had been planted in a "clear cut" zone that had already started to reforest itself with tan oak and madrone. Site A was sprayed with the fertilizer composition and revisited every six months for two years. A similar site ¼quarter of a mile away which was being managed by the same lumber company in a traditional manner was observed at the same time. After six months, the trees on site A had doubled in size. The tan oak and madrone had withered and died. It was noted that not only were the trees healthy, but the vegetation associated with "the old forest floor" prior to the clear cut had returned. The site similar to site A ¼mile away was managed in the traditional way. The managers of the Douglas Fir plantation had found it necessary to spray the competing "tenting" trees, tan oak and madrone, with Round Up (a herbicide) to preserve the growth of the Douglas Fir. It was also noted that very little active vegetation was present due to the use of the herbicide. Erosion was a factor in a 22% loss of the original plantation of the Douglas Fir. Average growth of the plantation trees was 50% less than growth averages on site A.

On all of the visits back to site A over a two year period of time, similar observations were made. Site A enjoyed a complete recovery without any further applications while the similar site managed by the lumber company had to be repeatedly defoliated with Round Up to prevent tenting on the unfertilized ground.

Site B was a quarter acre site located in Rome, Me. Site B containing a planting of white pine and balsm fir rooted in rocky soil. A similar site was planted with the same species. Site B was sprayed with the acidulated PPC fertilizer composition. The similar site was not treated. Both sites were observed for two years.

Site B showed significant growth with little competition from the usual broad leaved trees that shade out and compete in reforestation attempts with white pine and balsm fir. The trees grew at a rapid pace showing no signs of disease or beetle infestation. Erosion did not occur and natural grasses thrived on the test site; however, on the similar area next to site B, it was observed that in the first year colonies of raspberries, red maple, white birch and oak had established themselves. Soil had eroded and what grass there was on the site was spotty and scattered. By the second year, the similar site was completely over grown with broad leaf trees and the with pine and balsm fir had failed.

EXAMPLE 13

A fertilizer composition consisting of 1% PPC, 1.5% phosphoric acid and 98.5% water was blended in an air driven mixer for 30 minutes and decanted into a 2,000 ml. glass container.

A second fertilizer solution was prepared from a commercial cut flower preservative "Rose Life" manufactured by Ampco Chemical Division, Broomfield, Colo., following their directions. The solution was decanted into a 2,000 ml. glass container.

A third 2,000 ml. glass container was prepared containing ordinary tap water from the city of Augusta, Me. water supply. Three dozen John F. Kennedy roses were cut from identical plants. Each cutting was uniform in size and bud formation and taken one inch above the first five leaf projection from the rose plants.

As the roses were cut, they were plunged into water and held for 48 hours at 39° F. at the end of the holding period; one inch was removed from the base of each stem. They were placed in the three containers in groups of twelve in each container. The roses were observed over a period of twelve days.

The roses that were held in just ordinary city tap water opened on the first day. They were fragrant and looked uniformly fresh. On the second day, 80% of the blooms had begun to slump. By the third day, they were shedding their petals and were discarded. It was noted that the fragrance of the roses was very good even on the third day.

The roses that were held in water treated by "Rose Life" resisted opening for two days. On the third day, three out of the twelve buds slightly opened. The fragrance was diminished. By the sixth day, half of the roses had discolored and had to be discarded. The remaining roses lasted two more days, but never fully opened nor did they have any significant fragrance.

The roses that were held in the PPC fertilizer solution opened slowly on the first day. The fragrance was excellent through the entire twelve day test. Though the second and seventh days they opened uniformity until they reached 90% of their full bloom on the ninth day. The test was held for three more days until the roses started to show slight signs of discoloration on the outer petals. Two of the twelve roses had to be removed on the ninth day of the test due to shedding of petals.

EXAMPLE 14

Two raised planting beds measuring 4×8 feet were constructed and filled with coarse washed sand. Bed A was treated with a PPC fertilizer composition containing 1% phosphoric acid, 7% urea prill, 1% PPC and 91% water. Bed B was treated with the commercial fertilizer "Miracle-Gro" (Stems Nurseries) following the instructions on the container. Both beds were planted with Swiss Chard (Burpeg Seed Co.) and watered equally in the morning and in the early evening during the growing season.

Bed A showed sustained growth with multiple harvests of good tasting Swiss Chard. Low weed and limited insect intrusion were noted. The second year planting showed slightly less yield with no additional fertilizer being applied other than the initial spraying from the previous year, but several harvests of good tasting Swiss Chard were obtained.

Bed B showed good early results, but had to be retreated with three subsequent applications of the Miracle-Gro to get a harvest. When the treatment was halted, the plants stopped producing Swiss Chard . Tasting the Swiss Chard produced in Bed B left a long lasting bitter taste in the mouth. The second years planting failed when no additional Miracle-Gro was added to Bed B. The surface of the bed became barren with the exception of minor weed growth.

EXAMPLE 15

A fertilizer composition was prepared using 10% nitrogen derived from diammonium phosphate, 52% available phosphoric acid derived from diammonium phosphate and monopotassium phosphate, 17% water soluble potash derived from monopotassium phosphate, 3% PPC and 18% organic filler. The fertilizer was dressed into a test site of one acre consisting of well drained, sandy soil that was planted with potatoes for two years without any other additional applications of fertilizer. The soil produced exceptional potatoes. It was noticed that weed control on the site was greatly diminished.

EXAMPLE 16

A fish emulsion fertilizer was prepared from a surimi extracted from the muscle tissue of herring and mackerel by washing the fish with a solution of acidulated PPC (FEF-Fish Pat) prior to the extraction. There was significantly less odor than is normally associated with fish emulsion products such as fertilizers. When the acidulated PPC fertilizer was side dressed into a test bed of John F. Kennedy rose bushes, the plants developed sturdy root systems and produced high quality flowers with only one application of the fertilizer during the first year of planting.

I claim:

1. A controlled release plant protection agent delivery composition for controlling a population of plants or related vegetation in dry, moist, semi-aquatic, or aquatic environments comprising: (a) at least one protein-polysaccharide complex composition comprising: between about 90% to 99.5% by weight of a water-soluble polysaccharide impregnated with between about 10% to 0.5% by weight of a substantially water-insoluble protein, and (b) at least one plant protection agent, said protein-polysaccharide complex and said plant protection agent being present in a total amount effective to control or fertilize a target population of vegetation or to control a target population of pests by ground or aerial application techniques. and wherein said composition is an admixture formed by mixing the protein-polysaccharide complex composition and the plant protection agent.

2. The composition of claim 1 wherein the water-soluble polysaccharide is selected from the group consisting of alginate, carrageenin, gum arabic, tragacanth, guar gum, pectin, ghatti, xanthan gum and mixtures thereof.

3. The composition of claim 1 wherein the substantially water-insoluble protein is a prolamine.

4. The composition of claim 1 wherein the substantially water-insoluble protein is zein.

5. The composition of claim 1 wherein the protein-polysaccharide complex composition further includes at least one additive for promoting impregnation of the water-soluble polysaccharide by the protein.

6. The composition of claim 1 wherein the plant protection agent is selected from the group consisting of a foliar nutrient, a herbicidal agent and a pesticidal agent and mixtures thereof.

7. The composition of claim 1 wherein the the weight ratio of protein-polysaccharide complex composition to the plant protection agent is from about 0.1:100 to about 100:0.001.

8. The composition of claim 1 wherein the water-soluble polysaccharide comprises guar gum and the substantially water-insoluble protein comprises zein.

9. The composition of claim 1 wherein the protein-polysaccharide complex composition further comprises between about 0.25% to 5% by weight of an acidulant.

10. The composition of claim 9 wherein the acidulant is selected from the group consisting of tannic acid, lactic acid, ascorbic acid, acetic acid, citric acid, malic acid, adipic acid, fumaric acid and mixtures thereof.

11. The composition of claim 1 wherein said delivery composition contains water at a protein-polysaccharide complex composition to water ratio of about 0.0001:100 to 1:20.

12. The controlled release plant protection agent delivery composition according to claim 1, wherein said composition is flowable and the weight ratio of proteinpolysaccharide complex composition to the plant protection agent is from about 0.1: 100 to about 100:0.001, the plant protection agent being incorporated in the flowable delivery composition for application at rates effective to control the target plants.

13. The controlled release plant protection agent delivery composition of claim 1, wherein the plant protection agent comprises at least one compound selected from the group consisting of herbicides, desiccants, algicides, defoliants, hormones, plant growth inhibitors, plant growth regulators, petroleum oils or solvent, sterilants, biological control agents, microbial control agents, pathogen, and parasites.

14. The composition of claim 1, further comprising at least one adjuvant, diluent or carrier oil, surfactant, alcohol, surface-active agent, or film-forming agent, with or without other additives such as water, binders, deflocculating agents, dispersing agents, penetrants, spreading agents, suspending agents, wetting agents, stabilizing agents, compatibility agents, sticking agents, waxes, inverting oils, co-solvents, coupling agents, foams, anti-foaming agents, synthetic plastics, elastomers, synergists, natural or synthetic polymers and other additives and mixtures thereof.

15. The composition of claim 14 wherein said oil, surfactant, surface-active agent or film-forming agent is a vegetable-or animal-base oil or fat within which the plant protection agent is soluble, suspendable or dispersable.

16. The controlled release plant protection agent delivery composition of claim 1, wherein the plant protection agent comprises: at least one pesticidal agent selected from the group consisting of insecticides, mosquitocides, molluscidies, schistomacides, avicides, larvicides, monomolecular films, duplex films, monolayers, petroleum oils, pupicides, biological control agents, pathogens, parasites, microbial control agents, insect growth regulators, conventional toxicants, chemosterilants, surface active agents, or film-forming agents, and mixtures thereof.

17. A herbicidal or pesticidal/herbicidal delivery composition for controlling a population of vegetation in dry, moist, semi-aquatic, or aquatic environments comprising: at least one protein-polysaccharide complex composition comprising: between about 90% to 99.5% by weight of a water-soluble polysaccharide impregnated with between about 10% to 0.5% by weight of a substantially water-insoluble protein, and at least one formulation containing a herbicidal or pesticidal/herbicidal agent dissolved, suspended, or dispersed in an oil, surfactant, film-forming agent, or surface active agent and/or water, said polymer and agent being present in a total amount effective to control a population of vegetation and/or habitat-related pests, by ground and/or aerial application techniques, and wherein said composition is an admixture formed by mixing the protein-polysaccharide complex and the dissolved, suspended or dispersed formulation containing a herbicidal or herbicidal/pesticidal agent.

18. The composition of claim 17, wherein the ratio of protein-polysaccharide complex to film-forming agent, surface active agent, surfactant, or oil is from about 0.1:1 to about 100:1.

19. The composition of claim 17 wherein the water-soluble polysaccharide is selected from the group consisting of alginate, carrageenin, gum arabic, tragacanth, guar gum, pectin, ghatti, xanthan gum and mixtures thereof.

20. The composition of claim 17 wherein the substantially water-insoluble protein is a prolamine.

21. The composition of claim 17, further comprising: at least one compound selected from the group consisting of herbicides, desiccants, algicides, defoliants, hormones, plant growth inhibitors, plant growth regulators, petroleum oils or solvents, sterilants, biological control agents, microbial control agents, pathogens, and parasites.

22. A method for controlling one or more population of plants without or in conjunction with other habitat-related pests comprising the steps of:

preparing a herbicidal or herbicidal/pesticidal delivery composition comprising at least one protein-polysaccharide complex composition comprising: between about 90% to 99.5% by weight of a water-soluble polysaccharide impregnated with between about 10% to 0.5% by weight of a substantially water-insoluble protein, and at least one formulation containing a herbicidal or herbicidal/pesticidal agent; and forming an admixture of said protein-polysaccharide complex composition and said formulation containing a herbicidal or herbicidal/pesticidal agent; and applying said herbicidal or herbicidal/pesticidal delivery composition in an amount effective to control the population of plants or habitat related pests to a dry, moist, semi-aquatic, or aquatic environment area needing plant control treatment or simultaneous plant and pest control treatment.

23. The method of claim 22 wherein the water-soluble polysaccharide is selected from the group consisting of alginate, carrageenin, gum arabic, tragacanth, guar gum, pectin, ghatti, xanthan gum and mixtures thereof.

24. The method of claim 22 wherein the substantially water-insoluble protein is a prolamine.

25. The method of claim 22 wherein the substantially water-insoluble protein is zein.

26. The method of claim 22 wherein the protein-polysaccharide complex composition further includes at least one additive for promoting impregnation of the water-soluble polysaccharide by the protein.

27. The method of claim 22 wherein the protein-polysaccharide complex composition further comprises between about 0.25% to 5% by weight of an acidulant.

28. The method of claim 22 wherein the acidulant is selected from the group consisting of citric acid, tannic acid, lactic acid, ascorbic acid, acetic acid, malic acid, adipic acid, fumaric acid and mixtures thereof.

29. The method of claim 22, further comprising the step of premixing the delivery composition with at least one compound selected from the group consisting of herbicides, desiccants, algicides, defoliants, hormones, plant growth inhibitors, plant growth regulators, plant nutrients, petroleum oils or solvents, sterilants, biological control agents, microbial control agents, pathogens, parasites, insecticides, mosquitocides, schistomacides, molluscicides, avicides, larvicides, pupicides, monomolecular films, duplex films, monolayers, petroleum oils, biological control agents, pathogens, parasites, microbial control agents, insect growth regulators, conventional toxicants, chemosterilants, surface-active agents, film-forming agents, binders, deflocculating agents, dispersing agents, penetrants, spreading agents, suspending agents, wetting agents, compatibility agents, sticking agents, waxes, inverting oils, co-solvents, coupling agents, foams, anti-foaming agents, synthetic plastics, elastomers, synergists, natural or synthetic polymers and mixtures thereof.

30. The method of claim 22 further comprising, prior to applying to said dry, moist, semi-aquatic, or aquatic environment area, agglomerating said protein-polysaccharide complex composition and said formulation containing a herbicidal or herbicidaupesticidal agent, to produce granules, pellets, briquets, or other various shaped solid herbicidal or herbicidal/pesticidal delivery compositions.

31. The method of claim 22, wherein the composition is incorporated on or into dry or moist soil.

32. The method of claim 22 wherein the composition includes a hydrophilic oil, surfactant, surface-active agent, or film-forming agent, to control the herbicidal or herbicidal/pesticidal release rate.

33. A controlled release pesticidal delivery composition for controlling a population of insects comprising: (a) at least one protein-polysaccharide complex composition comprising: between about 90% to 99.5% by weight of a water-soluble polysaccharide impregnated with between about 10% to 0.5% by weight of a substantially water-insoluble protein, and (b) at least one formulation containing a pesticidal agent, said protein-polysaccharide complex and said pesticidal agent being present in a total amount effective to control a target population of pests by ground or aerial application techniques, and wherein said composition is an admixture formed by mixing the protein-polysaccharide complex composition and the formulation containing a pesticidal agent.

34. A foliar nutrient delivery composition for fertilizing a population of plants or related vegetation in dry, moist, semi-aquatic, or aquatic environments or preserving cut flowers comprising: (a) at least one protein-polysaccharide complex composition comprising: between about 90% to 99.5% by weight of a water-soluble polysaccharide impregnated with between about 10% to 0.5% by weight of a substantially water-insoluble protein, and (b) at least one formulation containing a foliar nutrient, said foliar nutrient being present in a total amount effective to fertilize or preserve a target population of vegetation or flowers and wherein said composition is an admixture formed by mixing the protein-polysaccharide complex composition and the formulation containing a foliar nutrient.

35. The foliar nutrient delivery composition of claim 32, further comprising at least one compound selected from the group consisting of herbicides, desiccants, algicides, defoliants, hormones, plant growth inhibitors, plant growth regulators, petroleum oils or solvents, sterilants, biological control agents, microbial control agents, pathogens, parasites, insecticides, mosquitocides, schistomacides, molluscicides, avicides, larvicides, pupicides, monomolecular films, duplex films, monolayers, petroleum oils, biological control agents, pathogens, parasites, microbial control agents, insect growth regulators, conventional toxicants, chemosterilants, surface-active agents, film-forming agents, binders, deflocculating agents, dispersing agents, penetrants, spreading agents, suspending agents, wetting agents, compatibility agents, sticking agents, waxes, inverting oils, co-solvents, coupling agents, foams, anti-foaming agents, synthetic plastics, elastomers, synergists, natural or synthetic polymers and mixtures thereof.

36. The foliar nutrient delivery composition of claim 34, wherein the foliar nutrient comprises nitrogenous fertilizers, phosphate fertilizers, potassium fertilizers or mixtures thereof.

37. A method of preserving cut flowers comprised of forming an aqueous solution containing (a) at least one protein-polysaccharide complex composition comprising: between about 90% to 99.5% by weight of a water-soluble polysaccharide impregnated with between about 10% to 0.5% by weight of a substantially water-insoluble protein, and (b) at least one foliar nutrient, said foliar nutrient being present in a total amount effective to preserve a target population of cut flowers and inserting cut flowers therein.

* * * * *